United States Patent [19]

Shimizu et al.

[11] Patent Number: 4,487,752
[45] Date of Patent: Dec. 11, 1984

[54] METHOD FOR PRODUCING IODINE OR IODINE DERIVATIVES

[75] Inventors: Atsushi Shimizu; Kazunori Yamataka, both of Nobeoka, Japan

[73] Assignee: Asahi Kasei Kogyo Kabushiki Kaisha, Osaka, Japan

[21] Appl. No.: 521,232

[22] Filed: Aug. 8, 1983

[30] Foreign Application Priority Data

Aug. 10, 1982 [JP] Japan ............................. 57-137850
Aug. 11, 1982 [JP] Japan ............................. 57-138376
Oct. 20, 1982 [JP] Japan ............................. 57-182986
Oct. 20, 1982 [JP] Japan ............................. 57-182987

[51] Int. Cl.$^3$ ............................................. C01B 7/14
[52] U.S. Cl. ................................................. 423/507
[58] Field of Search ..................................... 423/507

[56] References Cited

U.S. PATENT DOCUMENTS 3,103,419  9/1963  Hunter et al. ............... 423/507
3,975,439  8/1976  Klabunde ..................... 260/581
4,410,505 10/1983  O'Keefe et al. ............. 423/507

FOREIGN PATENT DOCUMENTS 53-50122   5/1978  Japan .
53-73489   6/1978  Japan .
53-132530 11/1978  Japan .

OTHER PUBLICATIONS

*J. Chim. Phys.*, 55, 407, (1958).
*J. C. S.*, Dalton, 793, (1974).
*Organic Syntheses*, 2, 347, (1943).

Primary Examiner—Howard S. Williams
Attorney, Agent, or Firm—Armstrong, Nikaido, Marmelstein & Kubovcik

[57] ABSTRACT

A method for producing iodine or iodine derivatives which comprises oxidizing ammonium iodide with oxygen or oxygen-containing gas in a medium comprising a transition metal compound, a weak acid and water to produce the iodine or iodine derivatives.

The iodine and iodine derivatives are useful as medical and agricultural chemicals, dyes, pigments, intermediates thereof and the like.

18 Claims, No Drawings

METHOD FOR PRODUCING IODINE OR IODINE DERIVATIVES

The present invention relates to a method for producing iodine or iodine derivatives from ammonium iodide as a material.

Iodine is a useful compound finding a wide application in intermediates for organic synthesis, catalysts, medicines, health medicines, microbicides, additives for livestock feeds, stabilizers for organic compounds, dyes, photomechanical processes, agricultural chemicals, refining of rare metals, analytical reagents and the like.

Also, various iodine derivatives are useful compounds finding a wide application as intermediates for the synthesis of dyes, pigments, medicines, agricultural chemicals and the like. For example, p-iodoaniline is important as a material for the synthesis of p-phenylenediamine which is a monomer for aramide fibers.

Generally, iodine is obtained from Chile nitre or salt water naturally occurring together with a natural gas. Industrially, iodine is obtained in many cases by a method to oxidize iodine anions contained in salt water with aqueous copper(II) sulfate or iron(II) sulfate solutions. Since this method is generally carried out in a strongly acidic condition, salts of a strong acid with a strong alkali such as sodium sulfate, etc. are produced as by-product, and treatment of the salts becomes a problem.

As a method to obtain iodine from ammonium iodide, there are given an electrolytic method (U.S. Pat. No. 3,975,439), a method with cupric compounds [Japanese Patent Application Kokai (Laid-open) No. 50122/1978], an oxidizing method with oxygen [Japanese Patent Application Kokai (Laid-open) No. 73489/1978] and the like.

In the electrolytic method (U.S. Pat. No. 3,975,439), the reaction is carried out in a dilute solution and a membrane is necessary, so that the apparatus becomes of a large scale. Besides, large quantities of electric power are consumed, so that this method may not be said to be an advantageous one in industry. In the method with cupric compounds [Japanese Patent Application Kokai (Laid-open) No. 50122/1978], this reaction is stoichiometric so that the cupric compound does not act as a catalyst. This method is therefore disadvantageous to produce large quantities of iodine. In the oxidizing method with oxygen [Japanese Patent Application Kokai (Laid-open) No. 73489/1978], iodine is obtained by oxidizing ammonium iodide with oxygen in an aqueous ammonia solution using a copper compound as catalyst. In the oxidation of iodide ions, a strong acid is necessary in general [J. Chim. Phys., 55, 407 (1958); JCS, Dalton, 793 (1974)]. In this method, however, the iodine-forming reaction is carried out in ammoniacal alkaline conditions, so that the rate of iodine production is extremely slow. Besdies, since this iodine production is accompanied by ammonia production, the reaction is presumed to become further slower. Also, the reaction in ammoniacal alkaline conditions, as apparent from A Comprehensive Treatise on Inorganic and Theoretical Chemisty, 8, 606 (1928) published by Longmans, Green & Col, Ltd. and the like, is easy to produce explosive nitrogen iodide, so that this method may not be said to be advantageous in industry.

As a method to produce iodine derivatives with ammonium iodide, for example a method to produce p-iodoaniline is known. In this method, p-iodoaniline is produced by reacting aniline with ammonium iodide in oxidizing conditions, but, for forming this oxidizing condition, there are known for example an electrolytic method (specification of U.S. Pat. No. 3,975,439), a method with cupric compounds [Japanese Patent Application Kokai (Laid-open) No. 50122/1978], an oxidizing method with oxygen [Japanese Patent Application Kokai (Laid-open) No. 132530/1978] and the like.

In the electrolytic method, however, it is necessary to carry out the reaction in a dilute solution and besides to use a membrane, so that the apparatus becomes of a large scale and large quantities of electric power are consumed. It may be said, therefore, that this method is not always advantageous when it is applied on an industrial scale.

In the method with cupric compounds, the cupric compound does not act as a catalyst, and this reaction is carried out stoichiometrically, so that large quantities of cupric compound are required. This method is therefore disadvantageous as an industrial one.

In the oxidizing method with oxygen, a reaction step in which iodine is generated by oxidizing ammonium iodide in an aqueous ammonia solution in the presence of a copper compound catalyst, and a reaction step in which the generated iodine is reacted with aniline, should be carried out in seaparate reactors, so that it is unavoidable that this method is disadvantageous in terms of apparatus and operation. A reason why this reaction should be carried out in two steps may be considered to be due to that there is a possibility for aromatic amino compounds to dimerize into azobenzene in general in the presence of oxygen, copper compounds and bases [Bull. Chem. Soc. Japan, Vol. 32, p. 780 (1959)]. Also, in the oxidation of iodide ions, strong acids are required in general [J. Chim. Phys., 55, 407 (1958); JCS, Dalton, 793 (1974)]. In the foregoing method, however, iodine is produced in ammoniacal alkaline conditions, so that the rate of iodine production is slow. In addition, since ammonia is produced as by-product together with the iodine production, the reaction becomes further slower.

Besides, in the first step of this method, iodine is treated in ammoniacal alkaline conditions, so that there is a fear of an explosive nitrogen iodide being produced in such condition [A Comprehensive Treatise on Inorganic and Theoretical Chemistry, 8, 606 (1928), published by longmans, Green & Co., Ltd.]. Consequently, this method has also a defect that it is dangerous.

When the functional group is hydroxyl, that is with phenols, an iodinating reaction is generally carried out in aqueous alkali solutions, but, for reasons that alkali iodide such as KI, NaI, etc. is produced as by-product, the alkali salt of phenol needs to be converted into phenol, and that the waste aqueous solution from the reaction needs to be neutralized, it may be said that this method is not always advantageous in industry.

As a result of an extensive study to overcome these defects of the conventional methods, and to develop an advantageous commercial method which enables iodine and iodine derivatives to be obtained in good yields and besides, produces no by-products which are difficult to regenerate, the present inventors found that, in media containing a transition metal compound and a weak acid, iodine can be obtained by oxidizing ammonium iodide with oxygen, and besides, that the iodine can satisfactorily be reacted with functional group-containing compounds without producing by-products such as nitrogen iodide, azobenzenes, alkali iodides and the like. The present invention was completed based on this finding.

According to the present invention, there is provided a method for producing iodine and iodine derivatives characterized in that, in media containing a transition metal compound, a weak acid and water, ammonium iodide is oxidized with oxygen or an oxygen-containing gas.

Particularly, the present invention provides a markedly efficient method for obtaining iodine and iodine derivatives in which a sufficient rate of iodine production can be obtained by using a weak acid, and in which, after taking the generated iodine out of the system by methods such as extraction or consumption by a proper reaction, the produced ammonium salt of the weak acid is thermally decomposed to recover the weak acid which is then re-used for the iodine-forming reaction.

Referring to the reaction of the present invention with reference to an example using a copper compound and ammonium dihydrogenphosphate, iodine is presumed to be produced based on the following reaction mechanism:

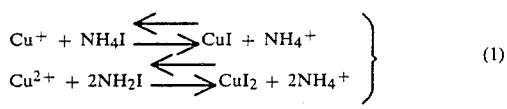

(1)

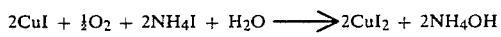

(2)

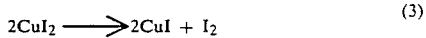

(3)

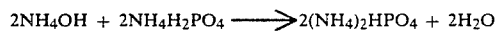

(4)

Further, reaction of iodine with aniline probably proceeds as follows:

(5)

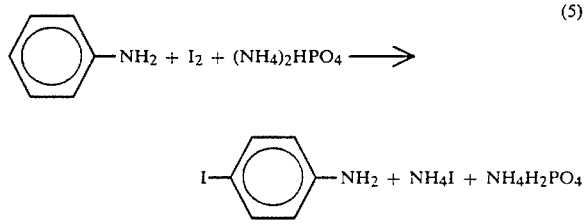

As described above, this reaction is a markedly efficient reaction in which diammonium hydrogenphosphate produced according to the reaction formula (4) acts as a base as shown in the reaction formula (5) to reproduce ammonium iodide and ammonium dihydrogenphosphate.

Generally, in the iodination of aromatic compounds such as aromatic amino compounds, in order to catch the produced hydrogen iodide, it is regarded as necessary to carry out the reaction in a weakly alkaline or alkaline condition [Org. Synth., 2, 347 (1943)]. Unexpectedly in the present invention, however, iodination of aromatic compounds proceeds without problems in the presence of a weak acid. This may be considered to be due to that the ammonium salt of the weak acid produced in the system acts as a base. According to the method of the present invention, therefore, oxidation of iodide ions and iodination need not be separated, thus making it possible to carry out the both reactions in the same system.

In alkaline conditions, generally, oxidation of iodide ions is slow, and alkali iodide which is difficult to re-use is produced, as described above. Particularly, in ammoniacal alkaline conditions, there is a fear of explosive nitrogen iodide being produced, and in combination of copper with aniline, there is a possibility of azobenzene being produced as by-product. In the method of the present invention, however, the oxidation proceeds rapidly, there is no fear of nitrogen iodide being produced and azobenzene is not also produced.

In the method of the present invention, a weak acid needs to be used, and if strong acid such as hydrochloric acid and sulfuric acid are used, nitrogen iodide is not produced but, with aromatic amino compounds, the iodination is inhibited by quaternarization of the nitrogen atom. Also, even though iodination of aromatic compounds occurred, the reaction does not proceed further more because the produced hydrogen iodide is not caught. Further in this case, the ammonium salt of the strong acid is produced, and it should be discarded, but when a weak acid is used, such a problem does not occur because the ammonium salt of the weak acid can thermally be decomposed into the weak acid and ammonia which are then recovered.

In alkaline conditions, as described above, progress of the oxidation is slow and also, in combination of a copper compound with an aniline, azobenzenes are easily produced in the presence of oxygen. Further in ammoniacal alkaline conditions, there is a fear of nitrogen iodide being produced. The method of such condition is therefore difficult to carry out in industry. While, in strong acidic conditions, practice of the method is difficult because the iodination is inhibited. The method of the present invention is a one having these problems solved by using a weak acid and a transition metal compound.

As the transition metal compound used in the present invention, any of those which are generally used as a catalyst for oxidation may be used. For example, compounds of Cu, Ag, V, Fe, Co, Ni, Cr, Mo, W, etc. may be used. Of these, Cu compounds and V compounds are particularly preferred because the rate of oxidation of iodine ion is high. In the reaction of the present invention, it is desirable to use at least one member selected from the foregoing transition metal compounds.

As the foregoing reaction formulae show, the metal compound used as a catalyst is simply regarded as the source of supply of metallic ions, while the kind of the anion part of the compound is not related to the reaction itself, and therefore, it may be regarded as not being particularly limited.

There is no particular limitation to the copper compound, and most copper compounds may be used. For example, cuprous iodide, cuprous chloride, cuprous oxide, cuprous bromide, cuprous cyanide, cuprous sulfate, cupric sulfate, cupric chloride, cupric hydroxide, cupric oxide, cupric bromide, cupric phosphate, cuprous nitrate, cupric nitrate, copper carbonate, cuprous acetate, cupric acetate and the like are preferred. Of these, CuCl, CuCl$_2$, CuBr, CuBr$_2$, CuI, CuO, Cu$_2$O, CuSO$_4$ and Cu(OCOCH$_3$)$_2$ are particularly preferred because they are easily available.

There is no particular limitation to the vanadium compound, and most vanadium compounds may be used. For example, vanadium monoxide, vanadium(II)

hydroxide, vanadium dichloride, vanadium(II) sulfate, $K_4[V(CN)_6]$, divanadium trioxide, vanadium(III) hydroxide, vanadium trifluoride, $M_2VF_5$ (M=Na, K, $NH_4$), vanadium trichloride, vanadium tribromide, vanadium triiodide, vanadium(III) sulfate, $MV(SO_4)_2$ (M=Na, K, $NH_4$), $K_3[V(CN)_6]$, vanadium dioxide, $M_2V_4O_9$ (M=Na, K, $NH_4$), vanadium tetrafluoride, $M_2[VOF_4(OH)_2]$ (M=Na, K, $NH_4$), vanadium tetrachloride, vanadium oxydichloride, vanadyl sulfate, $M_2[VO(SO_4)_2]$ (M=Na, K, $NH_4$), vanadium pentoxide, sodium metavanadate, potassium metavanadate, ammonium metavanadate, sodium orthovanadate, potassium orthovanadate, ammonium orthovanadate, sodium pyrovanadate, potassium pyrovanadate, ammonium pyrovanadate, sodium pentavanadate, potassium pentavanadate, ammonium pentavanadate, vanadium pentafluoride, $MVF_6$ (M=Na, K, $NH_4$), vanadium oxytrifluoride, vanadium oxytrichloride, vanadium oxytribromide, $VO_2Cl$ and the like are preferred. Of these, $V_2O_5$, $VOSO_4$, $VOCl_3$, $VOCl_2$, $VCl_3$, $NaVO_3$, $NH_4VO_3$ and $NaVO_4$ are particularly preferred because they are easily available.

There is no particular limitation to the iron compound, and most iron compounds may be used. Preferred ones are FeO, $Fe(OH)_2$, $Fe_2O_3$, FeO(OH), $FeCl_2$, $FeCl_3$, $FeBr_2$, $FeBr_3$, $FeI_2$, $Fe(NO_3)_2$, $Fe(NO_3)_3$, $FeSO_4$, $Fe_2(SO_4)_3$, $FeCO_3$, $Fe(CH_3CO_2)_2$, $Fe_3(PO_4)_2$, $FePO_4$ and the like.

There is no particular limitation to the cobalt compound, and most cobalt compounds may be used. Preferred ones are $CoCl_2$, $CoBr_2$, $CoI_2$, CoO, $Co(NO_3)_2$, $Co(NO_3)_3$, $CoSO_4$, $Co_2(SO_4)_3$, $CoCO_3$, $Co_3(PO_4)_2$, $Co(OH)_2$, $Co_3O_4 \cdot xH_2O$, $Co_2O_3 \cdot xH_2O$, $Co(CH_3CO_2)_2$ and the like.

There is no particular limitation to the nickel compound, and most nickel compounds may be used. Preferred ones are NiO, $Ni(OH)_2$, $NiCl_2$, $NiBr_2$, $NiI_2$, $Ni(NO_3)_2$, $NiSO_4$, $(NH_4)_2SO_4 \cdot NiSO_4 \cdot 6H_2O$, $NiCO_3 \cdot 6H_2O$, $Ni(CH_3CO_2)_2 \cdot 4H_2O$, $NiC_2O_4 \cdot 2H_2O$ and the like.

There is no particular limitation to the chromium compound, and most chromium compounds may be used. Preferred ones are CrO, $Cr_2O_3$, $CrO_3$, $CrO_5$, $CrCl_2$, $CrCl_3$, $CrBr_2$, $CrBr_3$, $CrI_2$, $CrI_3$, $Cr(SO_4)$, $Cr_2(SO_4)_3$, $Cr(OH)_2$, $Cr(NO_3)_3$, $Cr_3(PO_4)_2$, $CrPO_4$, $Cr(CH_3CO_2)_2$ and the like.

There is no particular limitation to the molybdenum compound, and most molybdenum compounds may be used. Preferred ones are $Mo(OH)_3$, $MoO_2$, $Mo_2O_5$, $MoO(OH)_3$, $MoO_3$, $MoCl_3$, $MoOCl$, $MoBr_3$, MoBr, $MoCl_4$, $MoBr_4$, $MoCl_5$, $MoOCl_3$, $MoOCl_4$, $MoO_2Cl_2$ and the like.

There is no particular limitation to the tungsten compound, and most tungsten compounds may be used. Preferred ones are $WO_2$, $WO_3$, $WCl_2$, $WBr_2$, $WI_2$, $WCl_4$, $WCl_5$, $WBr_5$, $WCl_6$, $WBr_6$, $WOCl_4$, $WO_2Cl_2$, $WOBr_4$, $WO_2Br_5$ and the like.

There is no particular limitation to the silver compound, and preferred ones are AgCl, AgBr, AgI, $Ag_2O$, $AgClO_4$, $AgClO_3$, $AgBrO_3$, $AgIO_3$, $Ag_2SO_4$, $Ag_2SO_3$, $Ag_2CrO_4$, $AgNO_3$, $Ag_3PO_4$, $Ag_3AsO_4$, $Ag_3AsO_3$, $Ag_2CO_3$, $Ag_2SiO_3$, $AgCH_3CO_2$, $Ag_2C_2O_4$, AgCN and the like.

These transition metal compounds may be used alone or in a mixture of two or more of them.

The amount of the transition metal compound used is not particularly limited, but amounts of $3 \times 10^{-4}$ to 0.3 mole per 100 g of water are preferred in terms of practical use. Also, the transition metal compound may be used in solution in aqueous media or not.

The amount of ammonium iodide used is not particularly limited, but a higher concentration of the iodide in aqueous media tends to accelerate the rate of iodine production. In terms of practical use, amounts of 10 to 200 g per 100 g of water are preferred.

As oxygen used, of course oxygen gas and even air are sufficient to achieve the object of the present invention. There is no particular limitation to the pressure or partial pressure of oxygen, but a higher pressure tends to accelerate the rate of iodine production. In terms of practical use, 0.2 to 10 atm. is preferred.

The rate of oxidation is faster as the temperature is higher, but too high temperatures decompose the ammonium salt of weak acid to increase the ammonia concentration of the system, as a result of which the oxidation becomes slow. Generally, the temperature is preferably between 20° C. and 100° C.

The weak acid is used for the purpose of accelerating the rate of oxidation and preventing the production of nitrogen iodide and azobenzene by reacting it with ammonia produced by the iodine-forming reaction thereby limiting the pH of the system to a lower level. Also, when the ammonium salt of the weak acid is present, it performs a role to catch hydrogen iodide produced by the iodination. It is also desirable, if necessary, to thermally decompose the produced ammonium salt of the weak acid, recover the weak acid and re-use the acid for the iodine-generating reaction. As the weak acid, any of those of which the ammonium salt is capable of releasing ammonia when heated, will do. For example, there may be given phosphoric acid, ammonium dihydrogenphosphate, sodium dihydrogenphosphate, potassium dihydrogenphosphate, inorganic acids such as boric acid, arsenic acid, chromic acid, telluric acid, silicic acid, vanadic acid, etc., organic acids such as acetic acid, propionic acid, etc. Of these, phosphoric acid, dihydrogenphosphate and the organic acids are preferred. Further, in the cases of ammonium dihydrogenphosphate, sodium dihydrogenphosphate and potassium dihydrogenphosphate, their ammonium salt, i.e. monohydrogenphosphate, when heated, releases a quantitative amount of ammonia in a short time, whereby it returns to the original dihydrogenphosphate. Consequently, these phosphates are particularly preferred.

For recovery of the weak acid in the present invention, it is satisfactorily achieved by taking the generated iodine out of the system by means of extraction with organic solvents (e.g. ether) or proper iodine-consuming reaction and then heating the aqueous medium containing the produced ammonium salt of the weak acid. The weak acid recovered here can be re-used as a raw material for the iodine-producing reaction, there being no special necessity to add the fresh weak acid for iodine generation. As to a temperature at which the ammonium salt of the weak acid is decomposed, a higher temperature is better to increase the decomposition rate and percent decomposition, and the temperature is preferably 100° C. to 210° C.

The medium in the present invention is such that at least a part of it is water. But, those coming into no substantial reaction with iodine in this system, for example benzene, chlorobenzene and the like, may be used together with water. The hydrogen ion concentration of the aqueous medium varies with the acid and condition used, so that it is not limited. But, a larger hydrogen ion concentration tends to accelerate the rate of iodine production. For obtaining iodine derivatives, it is sufficient to add a compound capable of reacting with iodine, for example aromatic compounds, to the medium.

The aromatic compounds used in the present invention are ones having an electron donating group. Of these, whose of which the Hammett's substituent constant ($\delta_p$) is $-0.25$ or less are preferred. As such aromatic compounds, those having an amino, N-alkylamino, N,N-dialkylamino, hydroxy, alkoxy or aryloxy group are more preferred. Particularly prerferred compounds are aniline, o-toluidine, m-toluidine, p-toluidine, N-methylaniline, N,N-dimethylaniline, N-methyl-o-toluidine, N,N-dimethyl-o-toluidine, N-methyl-m-toluidine, N,N-dimethyl-m-toluidine, N-methyl-p-toluidine, N,N-dimethyl-p-toluidine, phenol, o-cresol, m-cresol, p-cresol, 2,3-xylenol, 2,4-xylenol, 2,5-xylenol, 2,6-xylenol, 3,4-xylenol, 3,5-xylenol, 3,6-xylenol, thiophenol, anisole, methyl phenyl sulfide, α-naphthol, diphenyl ether, α-naphthylamine and the like.

In the present invention, these compounds may be supplied to the reaction system at any of the steps before, during and after the oxidation, or at two or more steps selected from these ones. In either case, an iodine derivative can be obtained. In the method of the present invention, therefore, a time to supply the aromatic compounds to the reaction system may optionally be selected. Particularly, when p-iodoaniline is required selectively, the object can be achieved by cooling the reactor after the oxidation and adding aniline to react with the generated iodine. Generally, a lower iodination temperature gives a better position selectivity, and iodination temperatures between 0° C. and 100° C. are preferred.

In the present invention, when aromatic hydroxy compounds are used, it is more preferred to supply said compounds to the reaction system after the iodine-generating reaction. When the oxidation and iodination are carried out at the same time, the phenol is oxidized to increase by-products.

According to the method of the present invention, as described above, the use of weak acid accelerates the production of iodine, gives good yields of iodine and iodine derivatives and also, makes it possible to obtain iodinated compounds, without a step to separate iodine. Further, the ammonium salt of weak acid resulting from the oxidation acts as a base, so that addition of a base, which is regarded as essential to the usual iodination, is not necessary and besides, azobenzenes, explosive nitrogen iodide and alkali iodides which are difficult to re-use are not produced.

It is also possible, as need arises, to recover the weak acid for re-use, or to recover ammonia for other uses which is generated simultaneously on the recovery of the weak acid. As described above, the method of the present invention is a very advantageous one for the production of iodine and iodine derivatives generating no industrial waste.

The present invention will be illustrated more specifically with reference to the following examples.

In the following examples, the yield of iodine was obtained from the equation (2), assuming that the oxidation follows the equation (1) below when ammonium dihydrogenphosphate is used as a weak acid:

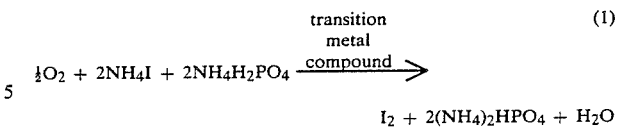

$$\tfrac{1}{2}O_2 + 2NH_4I + 2NH_4H_2PO_4 \xrightarrow{\text{transition metal compound}} \quad (1)$$

$$I_2 + 2(NH_4)_2HPO_4 + H_2O$$

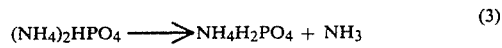

$$\text{Yield of iodine (\%)} = \frac{\text{mole number of generated iodine}}{\text{mole number of fed weak acid} \times \tfrac{1}{2}} \times 100 \quad (2)$$

The percent recovery of a weak acid was obtained from the equation (4), assuming that the thermal decomposition of the weak acid follows the equation (3) when ammonium dihydrogenphosphate is used as the weak acid:

$$(NH_4)_2HPO_4 \longrightarrow NH_4H_2PO_4 + NH_3 \quad (3)$$

$$\text{Percent recovery (\%)} = \frac{\text{mole number of generated ammonia}}{\text{mole number of the produced ammonium salt of the weak acid}} \times 100 \quad (4)$$

The yield of the iodine derivative was obtained from the following equation (5), provided that the reaction follows the equation (6).

$$\text{Yield (\%)} = \frac{\text{mole number of produced iodine derivative}}{\text{mole number of fed weak acid}} \times 100 \quad (5)$$

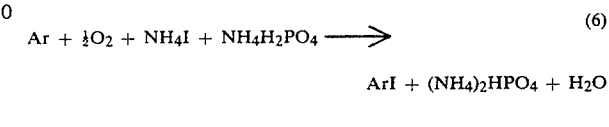

$$Ar + \tfrac{1}{2}O_2 + NH_4I + NH_4H_2PO_4 \longrightarrow \quad (6)$$

$$ArI + (NH_4)_2HPO_4 + H_2O$$

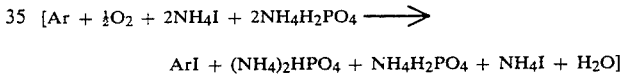

$$[Ar + \tfrac{1}{2}O_2 + 2NH_4I + 2NH_4H_2PO_4 \longrightarrow$$

$$ArI + (NH_4)_2HPO_4 + NH_4H_2PO_4 + NH_4I + H_2O]$$

When other weak acids were used, calculation was also carried out using the equations (2) and (4).

EXAMPLE 1

(1) Generation of Iodine

To a 500-ml pressure-proof glass autoclave were added 300 g (2.07 moles) of ammonium iodide, 5 g (0.0263 mole) of copper iodide, 100 g (0.870 mole) of ammonium dihydrogenphosphate and 200 ml of pure water, and reaction was carried out with stirring under a condition that the oxygen pressure be 2 to 5 kg/cm² (gauge pressure) and the temperature be 50° C. At the point when the oxygen pressure decreased from 5 kg/cm² to 2 kg/cm², oxygen was supplied again to 5 kg/cm². After 7 hours, the generated iodine was determined with 0.1N aqueous sodium thiosulfate solution to obtain a value of 77.3 g (0.305 mole). The yield of iodine was 70%.

(2) Recovery of Weak Acid

After adding 600 ml of pure water to the aqueous iodine solution obtained in (1), iodine was extracted with three 1-liter portions of ether to find that nearly all the generated iodine could be recovered. Thereafter, a trace amount of iodine remaining in the aqueous solution was reduced with sodium thiosulfate to obtain an aqueous solution containing no molecular iodine. This aqueous solution was added to a 1-liter SUS316 autoclave and stirred while heating to 170° C. to 210° C. in a nitrogen atmosphere, during which ammonia and steam were released from the nozzle at the upper part of the autoclave and passed through a condenser. Thus, about 600 cc of aqueous ammonia was obtained in 2 hours. The generated ammonia was determined with 1N aqueous sulfuric acid solution to obtain a value of 10.4 g (0.612 mole). The percent recovery of ammonia was 100%.

(3) Re-oxidation

To the aqueous solution obtained in (2) was added 88 g (0.607 mole) of ammonium iodide equivalent to the consumed ammonium, and using a pressure-proof glass autoclave, oxidation was carried out again under a condition that the oxygen pressure be 2 to 5 kg/cm$^2$ (gauge pressure) and the temperature be 50° C. As a result, iodine was obtained in a yield of 50% in 4 hours.

the beginning of reaction, but turned alkaline with the production of iodine. In Comparative example 2, nitrogen iodide was produced, and when it was dried, it exploded by a slight impact.

TABLE 1

| Example | | NH$_4$I (g) | Catalyst (g) | Weak acid (g) | H$_2$O (cc) | Benzene (cc) | Oxygen pressure (gauge) (kg/cm$^2$) | Temperature (°C.) | First yield of iodine (%) | Weak acid Percent recovery (%) | Temperature (°C.) | Second yield of iodine (%) |
|---|---|---|---|---|---|---|---|---|---|---|---|---|
| Example | 1 | 300 | CuI 5 | NH$_4$H$_2$PO$_4$ 100 | 200 | — | 2–5 | 50 | 70 (7 hr.) | 100 | 170–210 | 50 (4 hr.) |
| | 2 | 150 | CuI 5 | NH$_4$H$_2$PO$_4$ 50 | 100 | 100 | 5–8 | 70 | 62 (3.5 hr.) | 100 | 170–210 | 50 (1 hr.) |
| | 3 | 100 | CuI 1 | CH$_3$COOH 21 | 100 | 100 | 2–5 | 50 | 80 (4 hr.) | 30 | 150–180 | 20 (4 hr.) |
| | 4 | 75 | Cu$_2$O 3 | NH$_4$H$_2$PO$_4$ 25 | 50 | — | 5–8 | 70 | 50 (6 hr.) | 100 | 170–210 | 40 (5 hr.) |
| Comparative | 1 | 30 | CuI 1 | — | 20 | 20 | 10 | 40 | 5.2 × 10$^{-4}$ mole (4 hr.) | — | — | — |
| | 2 | 200 | Cu$_2$O 50 | — | 100 | — | 5 | 50 | 0.070 mole (16 hr.) | — | — | — |

EXAMPLES 2 TO 4

Using the composition shown in Table 1, reaction was carried out in the same manner as in Example 1. The results obtained are shown in Table 1.

COMPARATIVE EXAMPLES 1 AND 2

Using the composition shown in Table 1, reaction was carried out in the same manner as in (1) of Example 1 but using no weak acid on the oxidation. The amount of iodine produced was only below or about equal to the amount of catalyst used. The system was neutral at

EXAMPLES 5 TO 8

Using the composition shown in Table 2, reaction was carried out in the same manner as in Example 1. The results obtained are shown in Table 2.

EXAMPLES 9 TO 13

Using the composition shown in Table 2, reaction was carried out in the same manner as in (1) of Example 1. The results obtained are shown in Table 2.

TABLE 2

| Example | | NH$_4$I (g) | Catalyst (g) | Weak acid (g) | H$_2$O (cc) | Benzene (cc) | Oxygen pressure (gauge) (kg/cm$^2$) | Temperature (°C.) | First yield of iodine (%) | Weak acid Percent recovery (%) | Temperature (°C.) | Second yield of iodine (%) |
|---|---|---|---|---|---|---|---|---|---|---|---|---|
| Example | 5 | 150 | CuCl 3 | NH$_4$H$_2$PO$_4$ 50 | 100 | 100 | 5–8 | 70 | 60 (3.5 hr) | 100 | 170–210 | 55 (2.5 hr) |
| | 6 | 150 | CuCl$_2$ 5 | NH$_4$H$_2$PO$_4$ 50 | 100 | 100 | 5–8 | 70 | 63 (3.5 hr) | 100 | 170–210 | 55 (2.5 hr) |
| | 7 | 150 | CuBr 5 | CH$_3$COOH 26 | 100 | 100 | 5–8 | 50 | 75 (4 hr) | 30 | 150–180 | 20 (4 hr) |
| | 8 | 150 | CuSO$_4$ 5 | NH$_4$H$_2$PO$_4$ 50 | 100 | 100 | 5–8 | 70 | 60 (3.5 hr) | 100 | 170–210 | 50 (2.5 hr) |
| | 9 | 150 | CuBr$_2$ 5 | CH$_3$COOH 26 | 100 | 100 | 5–8 | 50 | 79 (4 hr) | — | — | — |
| | 10 | 150 | Cu(CH$_3$COO)$_2$ 5 | NH$_4$H$_2$PO$_4$ 50 | 100 | 100 | 5–8 | 70 | 60 (3.5 hr) | — | — | — |
| | 11 | 150 | CuO 3 | NH$_4$H$_2$PO$_4$ 50 | 100 | 100 | 5–8 | 70 | 52 (6 hr) | — | — | — |
| | 12 | 150 | CuI 5 | H$_3$PO$_4$ 43 | 100 | — | 5–8 | 70 | 88 (3.5 hr) | — | — | — |
| | 13 | 150 | CuI 5 | CH$_3$CH$_2$COOH 32 | 100 | — | 5–8 | 70 | 63 (3.5 hr) | — | — | — |

EXAMPLES 14 TO 20 AND 26 TO 28

Using the composition shown in Tables 3 and 4, reaction was carried out in the same manner as in Example 1. The results obtained are shown in Tables 3 and 4.

EXAMPLES 21 TO 25 AND 29 TO 31

Using the composition shown in Tables 3 and 4, reaction was carried out in the same manner as in (1) of Example 1. The results obtained are shown in Tables 3 and 4.

TABLE 3

| Example | NH$_4$I (g) | Catalyst (g) | Weak acid (g) | H$_2$O (ml) | Benzene (ml) | Oxygen pressure (gauge) (kg/cm$^2$) | Temperature (°C.) | First yield of iodine (%) | Weak acid Percent recovery (%) | Weak acid Temperature (°C.) | Second yield of iodine (%) |
|---|---|---|---|---|---|---|---|---|---|---|---|
| 14 | 75 | V$_2$O$_5$ 2.4 | NH$_4$H$_2$PO$_4$ 25 | 50 | 50 | 6–8 | 70 | 45 (4.5 hrs) | 100 | 170–210 | 40 (4.0 hrs) |
| 15 | 75 | VOSO$_4$ 4.3 | NH$_4$H$_2$PO$_4$ 25 | " | — | " | " | 30 (5.0 hrs) | 100 | " | 30 (5.0 hrs) |
| 16 | 75 | VOCl$_3$ 4.6 | NH$_4$H$_2$PO$_4$ 25 | " | — | " | " | 42 (4.5 hrs) | 100 | " | 42 (4.5 hrs) |
| 17 | 75 | VOCl$_2$ 4.6 | NH$_4$H$_2$PO$_4$ 25 | " | — | " | " | 35 (5.5 hrs) | 100 | " | 30 (5.0 hrs) |
| 18 | 75 | VCl$_3$ 4.2 | NH$_4$H$_2$PO$_4$ 25 | " | — | " | " | 58 (5.5 hrs) | 100 | " | 50 (5.0 hrs) |
| 19 | 75 | NaVO$_3$ 3.2 | NH$_4$H$_2$PO$_4$ 25 | " | — | " | 100 | 42 (5.3 hrs) | 100 | " | 40 (5 hrs) |
| 20 | 75 | V$_2$O$_5$ 2.4 | CH$_3$COOH 13 | " | 50 | " | 50 | 51 (5 hrs) | 33 | 130–180 | 15 (3 hrs) |
| 21 | 75 | NH$_4$VO$_3$ 3.1 | CH$_3$COOH 13 | " | 50 | " | " | 48 (5 hrs) | | | |
| 22 | 75 | Na$_3$VO$_4$ 4.9 | CH$_3$COOH 13 | " | 50 | " | 50 | 51 (5 hrs) | | | |
| 23 | 75 | NH$_4$VO$_3$ 3.1 | NH$_4$H$_2$PO$_4$ 25 | " | 50 | " | 70 | 40 (5.5 hrs) | | | |
| 24 | 75 | Na$_3$VO$_4$ 4.9 | NH$_4$H$_2$PO$_4$ 25 | " | 50 | " | " | 40 (5.5 hrs) | | | |

TABLE 4

| Example | NH$_4$I (g) | Catalyst (g) | Weak acid (g) | H$_2$O (ml) | Benzene (ml) | Oxygen pressure (gauge) (kg/cm$^2$) | Temperature (°C.) | First yield of iodine (%) | Weak acid Percent recovery (%) | Weak acid Temperature (°C.) | Second yield of iodine (%) |
|---|---|---|---|---|---|---|---|---|---|---|---|
| 25 | 75 | Fe$_2$O$_3$ 4.5 | NH$_4$H$_2$PO$_4$ 25 | 50 | 50 | 6–8 | 70 | 13 (6 hr) | — | — | — |
| 26 | 75 | CoO 4.5 | NH$_4$H$_2$PO$_4$ 25 | " | " | " | " | 13 (6 hr) | 100 | 170–210 | 10 (10 hr) |
| 27 | 75 | NiSO$_4$ 4.5 | CH$_3$COOH 13 | " | — | " | " | 19 (6 hr) | 35 | 150–180 | 4 (6 hr) |
| 28 | 75 | Cr(NO$_3$)$_3$ 4.5 | NH$_4$H$_2$PO$_4$ 25 | " | — | " | " | 16 (6 hr) | 100 | 170–210 | 11 (10 hr) |
| 29 | 75 | MoCl$_5$ 4.5 | H$_3$PO$_4$ 22 | " | — | " | " | 17 (6 hr) | — | — | — |
| 30 | 75 | H$_2$WO$_4$ 4.5 | CH$_3$COOH 13 | " | — | " | " | 15 (6 hr) | — | — | — |
| 31 | 75 | AgCl 4.5 | H$_3$PO$_4$ 22 | " | — | " | " | 13 (6 hr) | — | — | — |

EXAMPLE 32

To a 500-ml pressure-proof glass autoclave were added 150 g (1.03 mole) of ammonium iodide, 5 g (0.0262 mole) of copper iodide, 50 g (0.435 mole) of ammonium dihydrogenphosphate, 70 g (0.654 mole) of p-toluidine, 250 ml of benzene and 100 ml of pure water, and reaction was carried out with stirring under a condition that the oxygen pressure be 3 to 8 kg/cm$^2$ (gauge pressure) and the temperature be 70° C. At the point when the oxygen pressure decreased from 8 kg/cm$^2$ to 3 kg/cm$^2$, oxygen was supplied again to 8 kg/cm$^2$. After 3 hours, the organic layer was taken out, and 83.1 g (0.357 mole) of 2-iodo-4-methylaniline was obtained from this layer. The yield was 82%.

EXAMPLE 33

Using the material shown in Table 5, reaction was carried out in the same manner as in Example 32. The result obtained is shown in Table 5.

EXAMPLE 34

(1) Iodination

Using the composition shown in Table 5, reaction was carried out in the same manner as in Example 32. The result obtained is shown in Table 5.

(2) Recovery of Weak Acid

To the aqueous layer after reaction in (1) were added 30 g (0.322 mole) of aniline and 150 ml of benzene, followed by stirring at 50° C. for 2 hours in a nitrogen atmosphere (nitrogen pressure, 2 kg/cm$^2$). The lower layer was then taken out and washed with 100 ml of benzene to recover the aqueous layer. To this aqueous layer were added 100 ml of pure water and then again 10 g (0.108 mole) of aniline and 100 ml of benzene, and the mixture was stirred at 50° C. for 1 hour in a nitrogen atmosphere (nitrogen pressure, 2 kg/cm$^2$). After the aqueous layer was taken out and fed to a 500-ml SUS136 autoclave, 170 ml of pure water was added and then nitrogen gas was filled therein (pressure, 2 kg/cm$^2$). The contents of the autoclave were stirred at 170° to 210° C. to thermally decompose diammonium hydrogen-phosphate produced by the oxidation. At the same time, ammonia and steam were released from the nozzle at the upper part of the autoclave and passed through a condenser. Thus, about 300 ml of aqueous ammonia was obtained in 1 hour. The generated ammonia was determined with 1N aqueous sulfuric acid solution to obtain a value of 5.17 g (0.304 mole). The percent recovery of ammonium dihydrogenphosphate was 100%.

(3) Re-iodination

To the aqueous solution obtained in (2) was supplemented ammonium iodide by 44.1 g (0.304 mole) equal to the amount consumed in (1), and then 48 g (0.516 mole) of aniline and 100 ml of benzene were added. Reaction was then carried out at 50° C. with stirring at an oxygen pressure of 2 to 5 kg/cm². As a result, iodoaniline was obtained in a yield of 38% in 6 hours.

EXAMPLE 35

(1) Iodination

To a 500-ml pressure-proof glass autoclave were added 150 g (1.03 mole) of ammonium iodide, 5 g (0.0262 mole) of copper iodide, 50 g (0.435 mole) of ammonium dihydrogenphosphate, 100 ml of benzene and 100 ml of pure water, and iodine was then generated by stirring the mixture under a condition that the oxygen pressure be 3 to 8 kg/cm² (gauge pressure) and the temperature be 70° C. After 3 hours, the contents of the autoclave were cooled to room temperature, and 48 g (0.516 mole) of aniline was added and reacted with the generated iodine at room temperature for 2 hours with stirring. Thereafter, the organic layer was taken out, and 40.0 g (0.183 mole) of iodoaniline was obtained from this layer. The yield of iodoaniline was 42%, and the ratio of para isomer to ortho isomer (para/ortho) was 19.

(2) Recovery of Weak Acid

The weak acid was recovered in the same manner as in (2) of Example 34. The precent recovery was 100%.

(3) Re-iodination

To the aqueous solution obtained in (2) was supplemented ammonium iodide by 26.5 g (0.183 mole) equal to the amount consumed in (1), and 100 ml of benzene was added. Iodine was then generated at 70° C. for 2.5 hours. Thereafter, the reaction solution was cooled to room temperature, and 48 g (0.516 mole) of aniline was added. Reaction was then carried out at room temperature for 2 hours to obtain iodoaniline in a yield of 31%. The ratio of para isomer to ortho isomer (para/ortho) was 19.

EXAMPLES 36 AND 37

Using the material shown in Table 5, reaction was carried out in the same manner as in Example 34. The results obtained as shown in Table 5.

The yield of Example 37 is the one of aniline base.

COMPARATIVE EXAMPLE 3

Using the composition shown in Table 5, reaction was carried out in the same manner as in Example 32 but using no weak acid. As a result, the amount of iodoaniline produced was only below the amount of catalyst used, and formation of azobenzene was observed. The reaction system turned alkaline owing to ammonia produced by the oxidation.

TABLE 5

| Example | NH₄I (g) | Catalyst (g) | Weak acid (g) | Aromatic compound (g) | H₂O (ml) | Benzene (ml) | Temperature (°C.) | Oxygen pressure (kg/cm²) (gauge) | First yield (%) | Percent recovery of weak acid (%) | Second yield (%) | Formation ratio |
|---|---|---|---|---|---|---|---|---|---|---|---|---|
| 32 | 150 | CuI 5 | NH₄H₂PO₄ 50 | p-Toluidine 70 | 200 | 250 | 70 | 3–8 | 82 (3 hrs.) | — | — | — |
| 33 | 150 | Cu₂O 5 | CH₃COOH 26 | p-Toluidine 70 | 100 | 250 | 70 | 4–8 | 80 (4 hrs.) | — | — | — |
| 34 | 150 | CuI 2.5 | NH₄H₂PO₄ 50 | Aniline 48 | 100 | 100 | 50 | 2–5 | 70 (11 hrs.) | 100 (170°–210° C.) | 38 (6 hrs.) | para/ortho = 7 |
| 35 | 150 | CuI 5 | NH₄H₂PO₄ 50 | Aniline 48 | 100 | 100 | 70ᵃ/r.t.ᵇ | 3–8 | 42ᶜ (3 hrs.) | 100 (170°–210° C.) | 31ᶜ (2.5 hrs.) | para/ortho = 19 |
| 36 | 150 | CuI 5 | NH₄H₂PO₄ 50 | Aniline 48 | 100 | 100 | 70 | 3–8 | 88 (3 hrs.) | 100 (170°–210° C.) | 66 (2.5 hrs.) | para/ortho = 5 |
| 37 | 100 | CuI 1 | CH₃COOH 21 | Aniline 16 | 100 | 100 | 50 | 2–5 | 86ᵈ (4 hrs.) | 32 (150°–180° C.) | 48ᵈ (4 hrs.) | para/ortho = 11 |
| Comparative example 3 | 30 | CuI 1 | — | Aniline 10 | 20 | 20 | 40 | 10 | Iodoaniline 6 × 10⁻⁴ mole (5 hrs) Azobenzene 1.2 × 10⁻⁴ mole | | | para/ortho = 11 |

ᵃTemperature of generation of iodine.
ᵇTemperature of iodination.
ᶜPeriod of time required for generation of iodine.
ᵈYield of aniline base.
*Yield of azobenzene in Examples 32 to 37: ≃0%

EXAMPLES 38 TO 40

Using the composition shown in Table 6, reaction was carried out in the same manner as in Example 35. The results obtained are shown in Table 6.

EXAMPLES 41 TO 44

Using the composition shown in Table 6, reaction was carried out in the same manner as in Example 32. The results obtained are shown in Table 6.

EXAMPLES 45 AND 46

Using the composition shown in Table 6, reaction was carried out in the same manner as in (1) of Example 35. The results obtained are shown in Table 6.

TABLE 6

| Example | NH₄I (g) | Catalyst (g) | Weak acid (g) | Aromatic compound (g) | H₂O (ml) | Benzene (ml) | Temperature (°C.) | Oxygen pressure (kg/cm²) (gauge) | First yield (%) | Percent recovery of weak acid (%) | Second yield (%) | Formation ratio |
|---|---|---|---|---|---|---|---|---|---|---|---|---|
| 38 | 150 | CuCl 3 | NH₄H₂PO₄ 50 | Aniline 48 | 100 | 100 | 70$^a$/r.t.$^b$ | 5–8 | 40$^c$ (3 hrs) | 100 | 30 (2 hrs) | para/ortho = 19 |
| 39 | 150 | CuCl₂ 5 | NH₄H₂PO₄ 50 | Aniline 48 | 100 | 100 | 70$^a$/r.t.$^b$ | 5–8 | 40$^c$ (3 hrs) | 100 | 32 (2 hrs) | para/ortho = 19 |
| 40 | 150 | CuBr 5 | CH₃COOH 26 | Aniline 48 | 100 | 0 | 70$^a$/r.t.$^b$ | 5–8 | 45$^c$ (3 hrs) | 33 | 10 (2 hrs) | para/ortho = 20 |
| 41 | 150 | CuBr₂ 5 | CH₃COOH 26 | p-Toluidine 70 | 100 | 250 | 70 | 5–8 | 83 (4 hrs) | — | — | — |
| 42 | 150 | CuSO₄ 5 | NH₄H₂PO₄ 50 | p-Toluidine 70 | 100 | 250 | 70 | 5–8 | 80 (4 hrs) | — | — | — |
| 43 | 150 | Cu(CH₃COO)₂ 5 | NH₄H₂PO₄ 50 | p-Toluidine 70 | 100 | 250 | 70 | 5–8 | 80 (4 hrs) | — | — | — |
| 44 | 150 | CuO 3 | NH₄H₂PO₄ 50 | p-Toluidine 70 | 100 | 250 | 70 | 5–8 | 82 (4 hrs) | — | — | — |
| 45 | 150 | CuI 5 | H₃PO₄ 43 | Aniline 48 | 100 | 0 | 70$^a$/r.t.$^b$ | 5–8 | 43$^c$ (3 hrs) | — | — | para/ortho = 19 |
| 46 | 150 | CuI 5 | CH₃CH₂COOH 32 | Aniline 48 | 100 | 0 | 70$^a$/r.t.$^b$ | 5–8 | 38$^c$ (3 hrs) | — | — | para/ortho = 19 |

$^a$Temperature of generation of iodine.
$^b$Temperature of iodination.
$^c$Period of time required for generation of iodine.
*Yield of azobenzene in Examples 38 to 78 excepting 58 to 64 and 66 to 70: ≈ 0%.

EXAMPLES 47 TO 50

Using the composition shown in Table 7, reaction was carried out in the same manner as in Example 35. The results obtained are shown in Table 7.

EXAMPLES 51 TO 54

Using the composition shown in Table 7, reaction was carried out in the same manner as in Example 34. The results obtained are shown in Table 7.

EXAMPLES 55 TO 57

Using the composition shown in Table 7, reaction was carried out in the same manner as in Example 32. The results obtained are shown in Table 7.

EXAMPLE 58

Using the material shown in Table 8, reaction was carried out in the same manner as in Example 35. The result obtained is shown in Table 8.

EXAMPLES 59 TO 64

Using the material shown in Table 8, reaction was carried out in the same manner as in (1) of Example 35. The results obtained are shown in Table 8.

EXAMPLES 65 TO 71

Using the material shown in Table 9, reaction was carried out in the same manner as in Example 32. The results obtained are shown in Table 9.

TABLE 7

| Example | NH₄I (g) | Catalyst (g) | Weak acid (g) | Aromatic compound (g) | H₂O (ml) | Benzene (ml) | Temperature (°C.) | Oxygen pressure (kg/cm²) (gauge) | First yield (%) | Percent recovery of weak acid (%) | Second yield (%) | Formation ratio |
|---|---|---|---|---|---|---|---|---|---|---|---|---|
| 47 | 75 | V₂O₅ 2.4 | NH₄H₂PO₄ 25 | Aniline 24 | 50 | 100 | 70$^a$/10$^b$ | 2–8 | 32$^c$ (4.5 hr) | 100 (170°–210° C.) | 30 (4.5 hr) | para/ortho = 26 |
| 48 | 75 | VOSO₄ 4.3 | NH₄H₂PO₄ 25 | Aniline 24 | " | " | 70$^a$/10$^b$ | " | 21$^c$ (5.0 hr) | 100 (170°–210° C.) | 21 (5.0 hr) | para/ortho = 26 |
| 49 | 75 | VOCl₃ 4.6 | NH₄H₂PO₄ 25 | Aniline 24 | " | " | 70$^a$/10$^b$ | " | 30$^c$ (4.5 hr) | 100 (170°–210° C.) | 30 (4.5 hr) | para/ortho = 26 |
| 50 | 75 | VOCl₂ 4.6 | NH₄H₂PO₄ 25 | Aniline 24 | " | " | 70$^a$/10$^b$ | " | 24$^c$ (5.5 hr) | 100 (170°–210° C.) | 25 (5.5 hr) | para/ortho = 26 |
| 51 | 75 | VCl₃ 4.2 | NH₄H₂PO₄ 25 | Aniline 24 | " | " | 70 | " | 60 (8.0 hr) | 100 (170°–210° C.) | 60 (8.0 hr) | para/ortho = 5 |
| 52 | 75 | NaVO₃ 3.2 | NH₄H₂PO₄ 25 | Aniline 24 | " | 0 | 100 | " | 45 (8.0 hr) | 100 (170°–210° C.) | 45 (8.0 hr) | para/ortho = 4.5 |
| 53 | 75 | V₂O₅ 2.4 | CH₃COOH 13 | Aniline 24 | " | 0 | 50 | " | 50 (6 hr) | 33 | 15 (5 hr) | para/ortho = 7 |
| 54 | 75 | NH₄VO₃ 3.1 | CH₃COOH 13 | p-Toluidine 28 | " | 150 | " | " | 50 (7.5 hr) | " | 13 (7.5 hr) | — |
| 55 | 75 | Na₃VO₄ 4.9 | CH₃COOH 13 | p-Toluidine 28 | " | 150 | " | " | 50 (7.5 hr) | — | — | — |
| 56 | 75 | NH₄VO₃ 3.1 | NH₄H₂PO₄ 25 | p-Toluidine 28 | " | " | " | " | 43 (8.5 hr) | — | — | — |
| 57 | 75 | Na₃VO₄ 4.9 | NH₄H₂PO₄ 25 | p-Toluidine 28 | " | " | 70 | " | 40 (8.5 hr) | — | — | — |

$^a$Temperature of generation of iodine.
$^b$Temperature of iodination.
$^c$Period of time required for generation of iodine.

EXAMPLES 72 TO 78

Using the material shown in Table 10, reaction was carried out in the same manner as in Example 32. The results obtained are shown in Table 10.

TABLE 8

| Example | NH$_4$I (g) | Catalyst (g) | Weak acid (g) | Aromatic compound (g) | H$_2$O (ml) | Benzene (ml) | Temperature (°C.) | Oxygen pressure (kg/cm$^2$) (gauge) | First yield (%) | Percent recovery of weak acid (%) | Second yield (%) | Formation ratio |
|---|---|---|---|---|---|---|---|---|---|---|---|---|
| 58 | 75 | CuI 2.5 | NH$_4$H$_2$PO$_4$ 25 | Phenol 24 | 50 | 100 | 70$^a$/r.t.$^b$ | 2–8 | 40$^c$ (3 hr) | 100 (170°–210° C.) | 39 (3 hr) | para/ortho = 0.4 |
| 59 | 75 | V$_2$O$_5$ 2.4 | NH$_4$H$_2$PO$_4$ 25 | Phenol 24 | 50 | 100 | 70$^a$/r.t.$^b$ | " | 40$^c$ (5 hr) | — | — | para/ortho = 0.4 |
| 60 | 75 | CuI 2.5 | NH$_4$H$_2$PO$_4$ 25 | o-Cresol 27 | 50 | 100 | 70$^a$/r.t.$^b$ | " | 42$^c$ (3 hr) | — | — | para/ortho = 1 |
| 61 | 75 | V$_2$O$_5$ 2.4 | NH$_4$H$_2$PO$_4$ 25 | o-Cresol 27 | 50 | 100 | 70$^a$/r.t.$^b$ | " | 38$^c$ (5 hr) | — | — | para/ortho = 1 |
| 62 | 75 | CuI 2.5 | NH$_4$H$_2$PO$_4$ 25 | p-Cresol 27 | 50 | 100 | 70$^a$/r.t.$^b$ | " | 45$^c$ (3 hr) | — | — | — |
| 63 | 75 | CuI 2.5 | NH$_4$H$_2$PO$_4$ 25 | 2,6-Xylenol 31 | 50 | 100 | 70$^a$/r.t.$^b$ | " | 42$^c$ (3 hr) | — | — | — |
| 64 | 75 | V$_2$O$_5$ 2.4 | NH$_4$H$_2$PO$_4$ 25 | 2,6-Xylenol 31 | 50 | 100 | 70$^a$/r.t.$^b$ | " | 40$^c$ (5 hr) | — | — | — |

$^a$Temperature of generation of iodine.
$^b$Temperature of iodination.
$^c$Period of time required for generation of iodine.

TABLE 9

| Example | NH$_4$I (g) | Catalyst (g) | Weak acid (g) | Aromatic compound (g) | H$_2$O (ml) | Benzene (ml) | Temperature (°C.) | Oxygen pressure (kg/cm$^2$) (gauge) | First yield (%) | Percent recovery of weak acid (%) | Second yield (%) | Formation ratio |
|---|---|---|---|---|---|---|---|---|---|---|---|---|
| 65 | 75 | CuI 2.5 | NH$_4$H$_2$PO$_4$ 25 | N,N—dimethylaniline 32 | 50 | 100 | 70 | 2–8 | 85 (3.5 hr) | — | — | — |
| 66 | 75 | CuI 2.5 | NH$_4$H$_2$PO$_4$ 25 | Thiophenol 29 | 50 | 100 | 70 | " | 10 (5 hr) | — | — | — |
| 67 | 75 | CuI 2.5 | NH$_4$H$_2$PO$_4$ 25 | Anisole 28 | 50 | 100 | 70 | " | 5 (6 hr) | — | — | — |
| 68 | 75 | CuI 2.5 | NH$_4$H$_2$PO$_4$ 25 | Methyl phenyl sulfide 32 | 50 | 100 | 70 | " | 5 (6 hr) | — | — | — |
| 69 | 75 | CuI 2.5 | NH$_4$H$_2$PO$_4$ 25 | α-Naphthol 38 | 50 | 100 | 70 | " | 22 (5 hr) | — | — | — |
| 70 | 75 | CuI 2.5 | NH$_4$H$_2$PO$_4$ 25 | Diphenyl ether 38 | 50 | 100 | 70 | " | 4 (6 hr) | — | — | — |
| 71 | 75 | CuI 2.5 | NH$_4$H$_2$PO$_4$ 25 | α-Naphthylamine 37 | 50 | 100 | 70 | " | 54 (4 hr) | — | — | — |

TABLE 10

| Example | NH$_4$I (g) | Catalyst (g) | Weak acid (g) | Aromatic compound (g) | H$_2$O (ml) | Benzene (ml) | Temperature (°C.) | Oxygen pressure (kg/cm$^2$) (gauge) | First yield (%) | Percent recovery of weak acid (%) | Second yield (%) | Formation ratio |
|---|---|---|---|---|---|---|---|---|---|---|---|---|
| 72 | 75 | FeCl$_2$ 4.5 | NH$_4$H$_2$PO$_4$ 25 | Aniline 24 | 50 | 100 | 70 | 6–8 | 13 (6 hr) | — | — | — |
| 73 | 75 | CoBr$_2$ 4.5 | NH$_4$H$_2$PO$_4$ 25 | Aniline 24 | 50 | 100 | 70 | " | 10 (6 hr) | — | — | — |
| 74 | 75 | Ni(NO$_3$)$_2$ 4.5 | NH$_4$H$_2$PO$_4$ 25 | Aniline 24 | 50 | 0 | 70 | " | 15 (6 hr) | — | — | — |
| 75 | 75 | CrCl$_3$ 4.5 | NH$_4$H$_2$PO$_4$ 25 | Aniline 24 | 50 | 0 | 70 | " | 11 (6 hr) | — | — | — |
| 76 | 75 | MoO$_3$ 4.5 | NH$_4$H$_2$PO$_4$ 25 | p-Toluidine 28 | 50 | 100 | 70 | " | 10 (6 hr) | — | — | — |
| 77 | 75 | WO$_3$ 4.5 | NH$_4$H$_2$PO$_4$ 25 | p-Toluidine 28 | 50 | 100 | 70 | " | 8 (6 hr) | — | — | — |
| 78 | 75 | AgCl 4.5 | NH$_4$H$_2$PO$_4$ 25 | p-Toluidine 28 | 50 | 100 | 70 | " | 9 (6 hr) | — | — | — |

What is claimed is:

1. A method for producing iodine or iodine derivatives which comprises oxidizing amonium iodide with oxygen or oxygen-containing gas in a medium containing a transition metal compound, a weak acid and water to produce the iodine or iodine derivatives.

2. The method according to claim 1, wherein the transition metal compound is at least one member selected from the group consisting of iron, cobalt, nickel, chromium, molybdenum, tungsten, copper, silver and vanadium compounds.

3. The method according to claim 2, wherein the transition metal compound is at least one member selected from the group consisting of copper and vanadium compounds.

4. The method according to claim 3, wherein the copper compound is CuCl, CuCl$_2$, CuBr, CuBr$_2$, CuI, CuO, Cu$_2$O, CuSO$_4$ or Cu(OCOCH$_3$)$_2$.

5. The method according to claim 3, wherein the vanadium compound is V$_2$O$_5$, VOSO$_4$, VOCl$_3$, VOCl$_2$, VCl$_3$, NaVO$_3$, NH$_4$VO$_3$ or NaVO$_4$.

6. The method according to claim 1, wherein the weak acid is one member selected from the group consisting of phosphoric acid, dihydrogenphosphates and organic acids.

7. The method according to claim 6, wherein the dihydrogenphosphate is ammonium dihydrogenphosphate, sodium dihydrogenphosphate or potassium dihydrogenphosphate.

8. The method according to claim 1, wherein part of the weak acid is obtained by a thermal decomposition of ammonium salt of weak acid formed in the iodinating reaction.

9. The method according to claim 8, wherein the thermal decomposition is carried out at a temperature of 100° to 210° C.

10. The method according to claim 1, wherein a pressure of the oxygen or oxygen-containing gas is 0.2 to 10 atmospheric pressure.

11. The method according to claim 1, wherein the medium contains an aromatic compound having an electron donating group.

12. The method according to claim 11, wherein the electron donating group of the aromatic compound has a Hammett's substituent constant ($\delta p$) of $-0.25$ or less.

13. The method according to claim 12, wherein the aromatic compound has a group of amino, N-alkylamino, N,N-dialkylamino, hydroxy, alkoxy or aryl group.

14. The method according to claim 13, wherein the aromatic compound is aniline, o-toluidine, m-toluidine, p-toluidine, N-methylaniline, N,N-dimethylaniline, N-methyl-o-toluidine, N,N-dimethyl-o-toluidine, N-methyl-m-toluidine, N,N-dimethyl-m-toluidine, N-methyl-p-toluidine, N,N-dimethyl-p-toluidine, phenol, o-cresol, m-cresol, p-cresol, 2,3-xylenol, 2,4-xylenol, 2,5-xylenol, 2,6-xylenol, 3,4-xylenol, 3,5-xylenol, 3,6-xylenol, α-naphthylamine, α-naphthol, anisole, methyl phenyl sulfide or diphenyl ether.

15. The method according to claim 11, wherein the aromatic compound is added before the oxidizing reaction to produce the iodine derivative.

16. The method according to claim 11, wherein the aromatic compound is added after the oxidizing reaction to produce the iodine derivative.

17. The method according to claim 16, wherein the iodine derivative forming reaction is carried out at 0° to 100° C.

18. The method according to claim 1, wherein the oxidizing reaction is carried out at 20° to 100° C.

* * * * *